United States Patent
Eriksson et al.

(10) Patent No.: US 10,916,344 B2
(45) Date of Patent: Feb. 9, 2021

(54) UTILIZING A MACHINE LEARNING MODEL TO IDENTIFY ACTIVITIES AND DEVIATIONS FROM THE ACTIVITIES BY AN INDIVIDUAL

(71) Applicant: Accenture Global Solutions Limited, Dublin (IE)

(72) Inventors: Laetitia Cailleteau Eriksson, London (GB); Kar Lok Chan, London (GB); Faisal Ahmed Valli, London (GB); Christopher Paul Ashley, London (GB)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/191,363

(22) Filed: Nov. 14, 2018

(65) Prior Publication Data

US 2019/0156944 A1 May 23, 2019

Related U.S. Application Data

(60) Provisional application No. 62/590,077, filed on Nov. 22, 2017.

(51) Int. Cl.
*G16H 40/67* (2018.01)
*G16H 50/20* (2018.01)
(Continued)

(52) U.S. Cl.
CPC ........... *G16H 40/67* (2018.01); *A61B 5/11* (2013.01); *A61B 5/6898* (2013.01);
(Continued)

(58) Field of Classification Search
CPC ......... A61B 2034/2065; A61B 8/5223; G16H 10/60
See application file for complete search history.

(56) References Cited

U.S. PATENT DOCUMENTS 9,737,214 B2   8/2017  Proud et al.
2003/0182117 A1*  9/2003  Monchi ................ G10L 15/22
                                                  704/237
(Continued)

FOREIGN PATENT DOCUMENTS

WO    2014028888 A2    2/2014
WO    2016110804 A1    7/2016

OTHER PUBLICATIONS

Extended European Search Report for Application No. EP18207432.8, dated Dec. 21, 2018, 8 pages.

*Primary Examiner* — Reginald R Reyes
(74) *Attorney, Agent, or Firm* — Harrity & Harrity, LLP

(57) ABSTRACT

A device receives historical information associated with an individual to be monitored, wherein the historical information includes at least one of information associated with a health history of the individual, health histories of other individuals, activities of the individual, or activities of the other individuals. The device receives monitored information associated with the individual from one or more client devices associated with the individual, and pre-processes the monitored information to generate pre-processed monitored information that is understood by the trained machine learning model. The device processes the pre-processed monitored information, with a trained machine learning model, to identify one or more activities of the individual and one or more deviations from the one or more activities by the individual, and performs one or more actions based on the one or more activities of the individual and/or the one or more deviations from the one or more activities.

20 Claims, 12 Drawing Sheets

(51) Int. Cl.
G06K 9/62 (2006.01)
G10L 25/30 (2013.01)
G16H 50/30 (2018.01)
G16H 20/30 (2018.01)
A61B 5/00 (2006.01)
A61B 5/11 (2006.01)
G06Q 50/22 (2018.01)
G16H 10/60 (2018.01)
G06K 9/00 (2006.01)
A61B 5/021 (2006.01)
A61B 5/024 (2006.01)

(52) U.S. Cl.
CPC ........ *A61B 5/7267* (2013.01); *G06K 9/00335* (2013.01); *G06K 9/6262* (2013.01); *G06K 9/6269* (2013.01); *G06K 9/6274* (2013.01); *G06Q 50/22* (2013.01); *G10L 25/30* (2013.01); *G16H 10/60* (2018.01); *G16H 20/30* (2018.01); *G16H 50/20* (2018.01); *G16H 50/30* (2018.01); *A61B 5/0022* (2013.01); *A61B 5/021* (2013.01); *A61B 5/024* (2013.01); *A61B 5/1112* (2013.01); *A61B 5/4833* (2013.01); *A61B 5/681* (2013.01); *A61B 5/6803* (2013.01); *A61B 5/7275* (2013.01); *A61B 5/746* (2013.01); *A61B 2505/07* (2013.01)

(56) References Cited

U.S. PATENT DOCUMENTS

| | | |
|---|---|---|
| 2013/0245389 A1 | 9/2013 | Schultz et al. |
| 2013/0325603 A1* | 12/2013 | Shamir ............. G06Q 30/0255 705/14.52 |
| 2015/0326680 A1* | 11/2015 | Farahani ................ G06N 20/00 706/12 |
| 2016/0081620 A1* | 3/2016 | Narayanan ........... A61B 5/0205 600/483 |

* cited by examiner

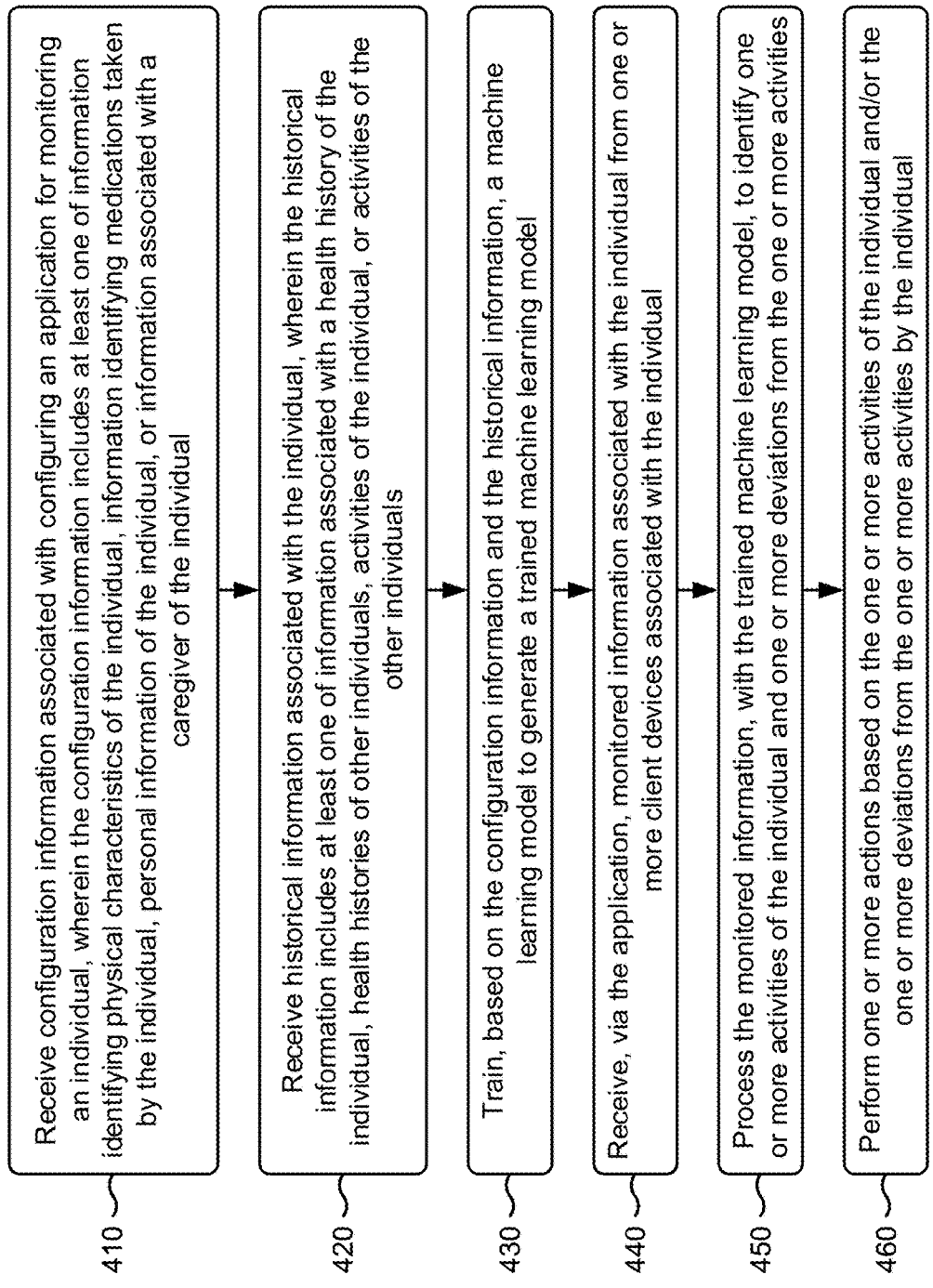

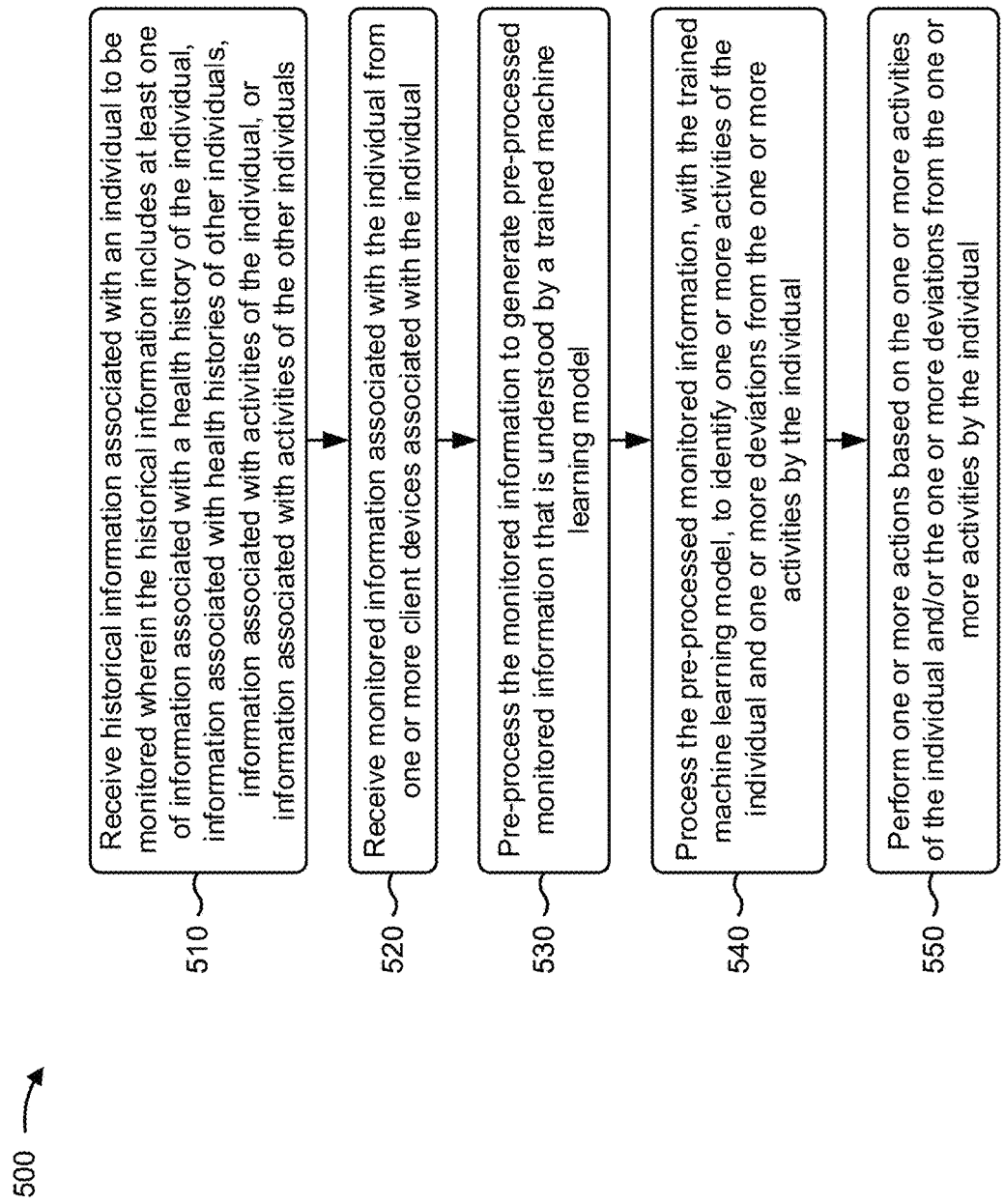

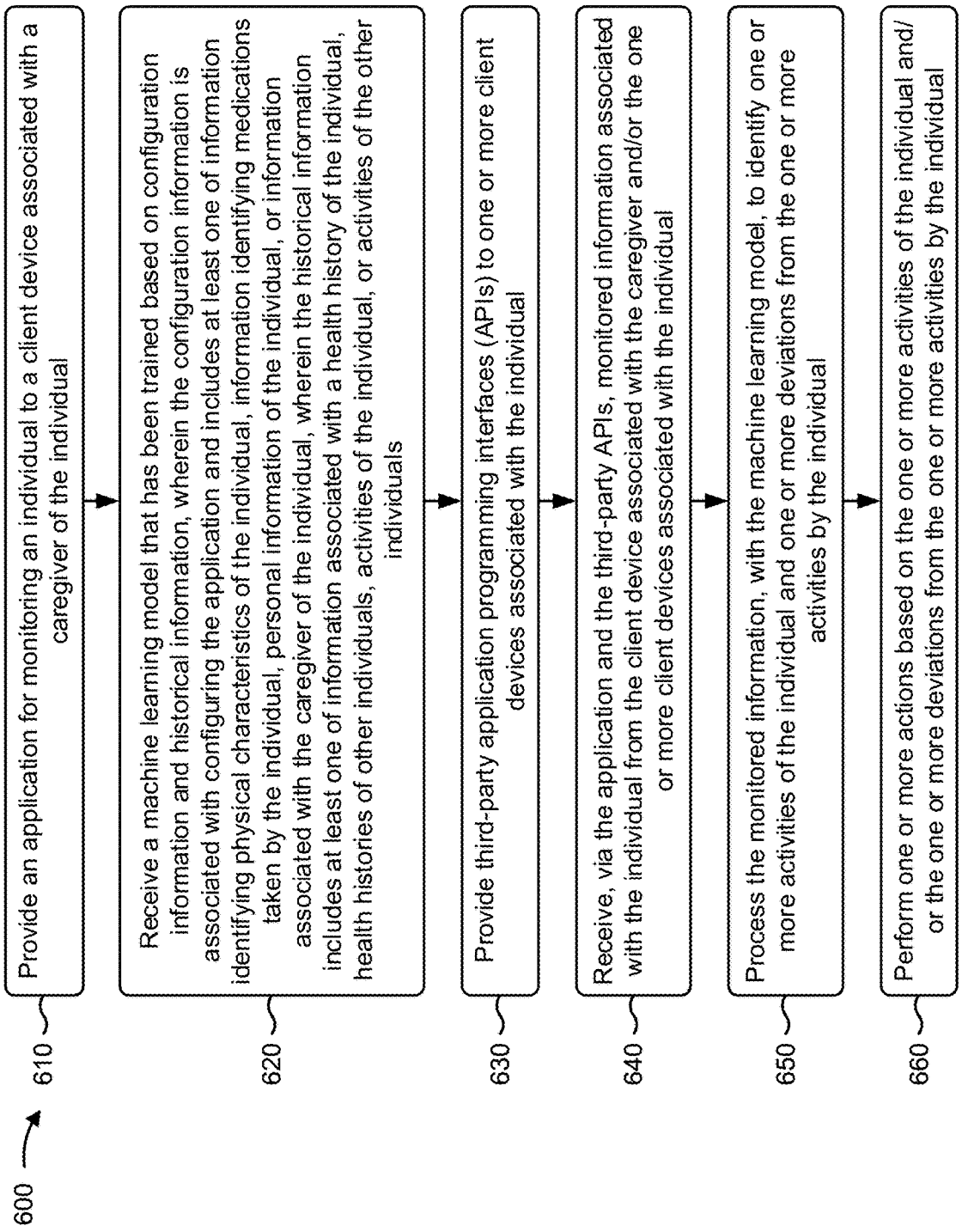

UTILIZING A MACHINE LEARNING MODEL TO IDENTIFY ACTIVITIES AND DEVIATIONS FROM THE ACTIVITIES BY AN INDIVIDUAL

RELATED APPLICATION

This application claims priority under 35 U.S.C. § 119 to U.S. Provisional Patent Application No. 62/590,077, filed on Nov. 22, 2017, the content of which is incorporated by reference herein in its entirety.

BACKGROUND

The population of people over the age of seventy-five is projected to double in the next thirty years. Thirty percent of elderly people (e.g., people older than a particular age, such as sixty-five) admit to speaking to less than one person a day, and loneliness has become a leading cause of depression for elderly people. Elderly care facilities are experiencing a funding crisis, and the number of elderly care facilities has been decreasing over the last five years. The remaining elderly care facilities struggle to find and retain staff, which impacts the quality of care provided to elderly people. The average fees for the elderly care facilities are expected to increase significantly, and many elderly people need to sell their homes in order to afford the elderly care facilities.

SUMMARY

According to some implementations, a method may include receiving configuration information associated with configuring an application for monitoring an individual, wherein the configuration information may include at least one of information identifying physical characteristics of the individual, information identifying medications taken by the individual, personal information of the individual, or information associated with a caregiver of the individual. The method may include receiving historical information associated with the individual, wherein the historical information may include at least one of information associated with a health history of the individual, information associated with health histories of other individuals, information associated with activities of the individual, or information associated with activities of the other individuals. The method may include training, based on the configuration information and the historical information, a machine learning model to generate a trained machine learning model, and receiving, via the application, monitored information associated with the individual from one or more client devices associated with the individual. The method may include processing the monitored information, with the trained machine learning model, to identify one or more activities of the individual and one or more deviations from the one or more activities by the individual, and performing one or more actions based on the one or more activities of the individual and/or the one or more deviations from the one or more activities by the individual.

According to some implementations, a device may include one or more memories, and one or more processors, communicatively coupled to the one or more memories, to receive historical information associated with an individual to be monitored, wherein the historical information may include at least one of information associated with a health history of the individual, information associated with health histories of other individuals, information associated with activities of the individual, or information associated with activities of the other individuals. The one or more processors may receive monitored information associated with the individual from one or more client devices associated with the individual, and may pre-process the monitored information to generate pre-processed monitored information that is understood by the trained machine learning model. The one or more processors may process the pre-processed monitored information, with a trained machine learning model, to identify one or more activities of the individual and one or more deviations from the one or more activities by the individual, and may perform one or more actions based on the one or more activities of the individual and/or the one or more deviations from the one or more activities by the individual.

According to some implementations, a non-transitory computer-readable medium may store instructions that include one or more instructions that, when executed by one or more processors of a device, cause the one or more processors to provide an application for monitoring an individual to a client device associated with a caregiver of the individual. The one or more instructions may cause the one or more processors to receive a machine learning model that has been trained based on configuration information and historical information, wherein the configuration information may be associated with configuring the application and may include at least one of information identifying physical characteristics of the individual, information identifying medications taken by the individual, personal information of the individual, or information associated with the caregiver of the individual, and wherein the historical information may include at least one of information associated with a health history of the individual, information associated with health histories of other individuals, information associated with activities of the individual, or information associated with activities of the other individuals. The one or more instructions may cause the one or more processors to provide third-party application programming interfaces (APIs) to one or more client devices associated with the individual, and receive, via the application and the third-party APIs, monitored information associated with the individual from the client device associated with the caregiver and/or the one or more client devices associated with the individual. The one or more instructions may cause the one or more processors to process the monitored information, with the machine learning model, to identify one or more activities of the individual and one or more deviations from the one or more activities by the individual, and perform one or more actions based on the one or more activities of the individual and/or the one or more deviations from the one or more activities by the individual.

BRIEF DESCRIPTION OF THE DRAWINGS

FIGS. 4-6 are flow charts of example processes for utilizing a machine learning model to identify activities and deviations from the activities by an individual.

DETAILED DESCRIPTION

Figure 1A:
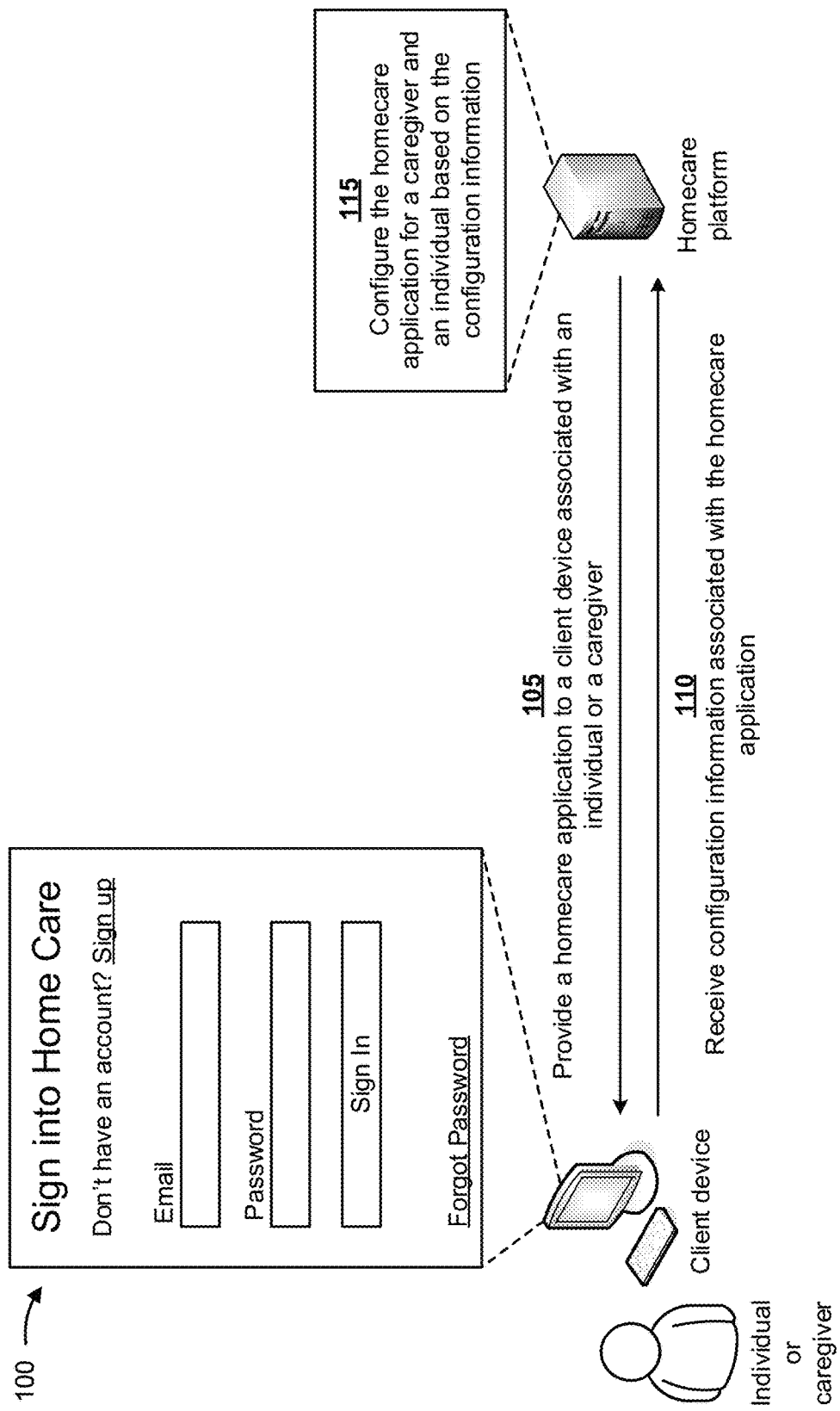
FIGS. 1A-1G are diagrams of an example implementation described herein.

The following detailed description of example implementations refers to the accompanying drawings. The same reference numbers in different drawings may identify the same or similar elements.

Many elderly people believe that there is a poor standard of care for elderly people in their own homes and the elderly care facilities. Most elderly people want to stay at home where research suggests that elderly people are happier, and their rate of degradation is reduced. However, current resources fail to provide adequate in-home care for elderly people at reasonable costs.

Some implementations described herein provide a homecare platform that utilizes a machine learning model to identify activities and deviations from the activities by an individual (e.g., an elderly person, a disabled person, an incapacitated person, and/or the like). For example, the homecare platform may receive historical information associated with an individual to be monitored, wherein the historical information may include at least one of information associated with a health history of the individual, information associated with health histories of other individuals, information associated with activities of the individual, or information associated with activities of the other individuals. The homecare platform may receive monitored information associated with the individual from one or more client devices associated with the individual, and may pre-process the monitored information to generate pre-processed monitored information that is understood by the trained machine learning model. The homecare platform may process the pre-processed monitored information, with a trained machine learning model, to identify one or more activities of the individual and one or more deviations from the one or more activities by the individual, and may perform one or more actions based on the one or more activities of the individual and/or the one or more deviations from the one or more activities by the individual.

In this way, the homecare platform improves the health and well-being of individuals by assisting individuals with everyday tasks so that the individuals stay connected and active in their homes. Further, the homecare platform enables resources (e.g., processing resources, memory resources, and/or the like) to be conserved that would otherwise be expended in caring for the individuals, such as resources provided by elderly care facilities, incapacitant care facilities, caregivers of the individuals, emergency personnel, and/or the like.

FIGS. 1A-1G are diagrams of an example implementation 100 described herein. As shown in FIGS. 1A-1G, a client device may be associated with an individual (e.g., an elderly person, a disabled person, an incapacitated person, and/or the like), a caregiver of the individual, and a homecare platform. As further shown in FIG. 1A, and by reference number 105, the homecare platform may provide a homecare application to the client device associated with the individual or the caregiver (herein after "individual/caregiver" will be used to refer to the individual, the caregiver, or collectively to the individual and the caregiver). In some implementations, the individual/caregiver may utilize the client device to download the homecare application from the homecare platform. In some implementations, the homecare platform may automatically provide the homecare application to the client device (e.g., without a request from the client device).

In some implementations, the individual/caregiver may utilize the client device to receive the homecare application from the homecare platform and may install the homecare application on the client device. The homecare application may enable the client device to monitor activities (e.g., a routine) of the individual, and provide the monitored activities to the homecare platform for determination of deviations from the activities of the individual, performance of one or more actions based on the deviations, and/or the like. In this way, the homecare application may enable a caregiver to monitor activities of an individual, may determine deviations from the activities of the individual, may improve the health and well-being of the individual by assisting the individual with everyday tasks so that the individual stays connected and active in their homes, and/or the like. In some implementations, the homecare application may execute on the client device, the homecare platform, other client devices, and/or the like.

As further shown in FIG. 1A, the homecare application may cause the client device to display a user interface for receiving configuration information, associated with configuring the homecare application, from the individual and/or the caregiver. In some implementations, if the individual is capable, the individual may utilize the client device to input the configuration information. In some implementations, if the individual is incapable, the caregiver may utilize the client device to input the configuration information. In some implementations, the configuration information may include information associated with a health (e.g., a height, a weight, physical maladies, mental illness, and/or the like) of the individual, medications taken by the individual, personal information (e.g., a home address, an email address, and/or the like) of the individual, information associated with the caregiver (e.g., personal information, contact information, and/or the like), credentials for accessing the homecare application (e.g., a username, an email address, a password, and/or the like), user preferences associated with the homecare application (e.g., preferred information displayed by the homecare application, a preferred language for the homecare application, etc.), and/or the like. In some implementations, the configuration information may include information associated with enabling the individual to invite a caregiver to help manage an account with the homecare platform on behalf of the individual, a first name of the caregiver, a last name of the caregiver, an email address of the caregiver, a telephone number of the caregiver, and/or the like.

As further shown in FIG. 1A, and by reference number 110, the homecare platform may receive the configuration information associated with the homecare application. In some implementations, the homecare platform may store the configuration information in a data structure (e.g., a database, a table, a list, and/or the like) associated with the homecare platform.

As further shown in FIG. 1A, and by reference number 115, the homecare platform may configure the homecare application for the caregiver and the individual based on the configuration information. For example, the homecare platform may utilize the configuration information to create accounts for the caregiver and the individual, to set preferences for the individual in the homecare platform, to create custom user interfaces for the individual and/or the caregiver, to provide recommendations to the individual and/or the caregiver, and/or the like. In some implementations, the homecare platform may receive the configuration information from the client device (e.g., prior to providing the homecare application to the client device), may configure the homecare application based on the configuration information, and may provide the configured homecare application to the client device. In some implementations, the client device may include a pre-configured homecare application, the individual/caregiver may install a pre-configured homecare application on the client device, the client device may configure the homecare application based on the configuration information, and/or the like.

Figure 1B:
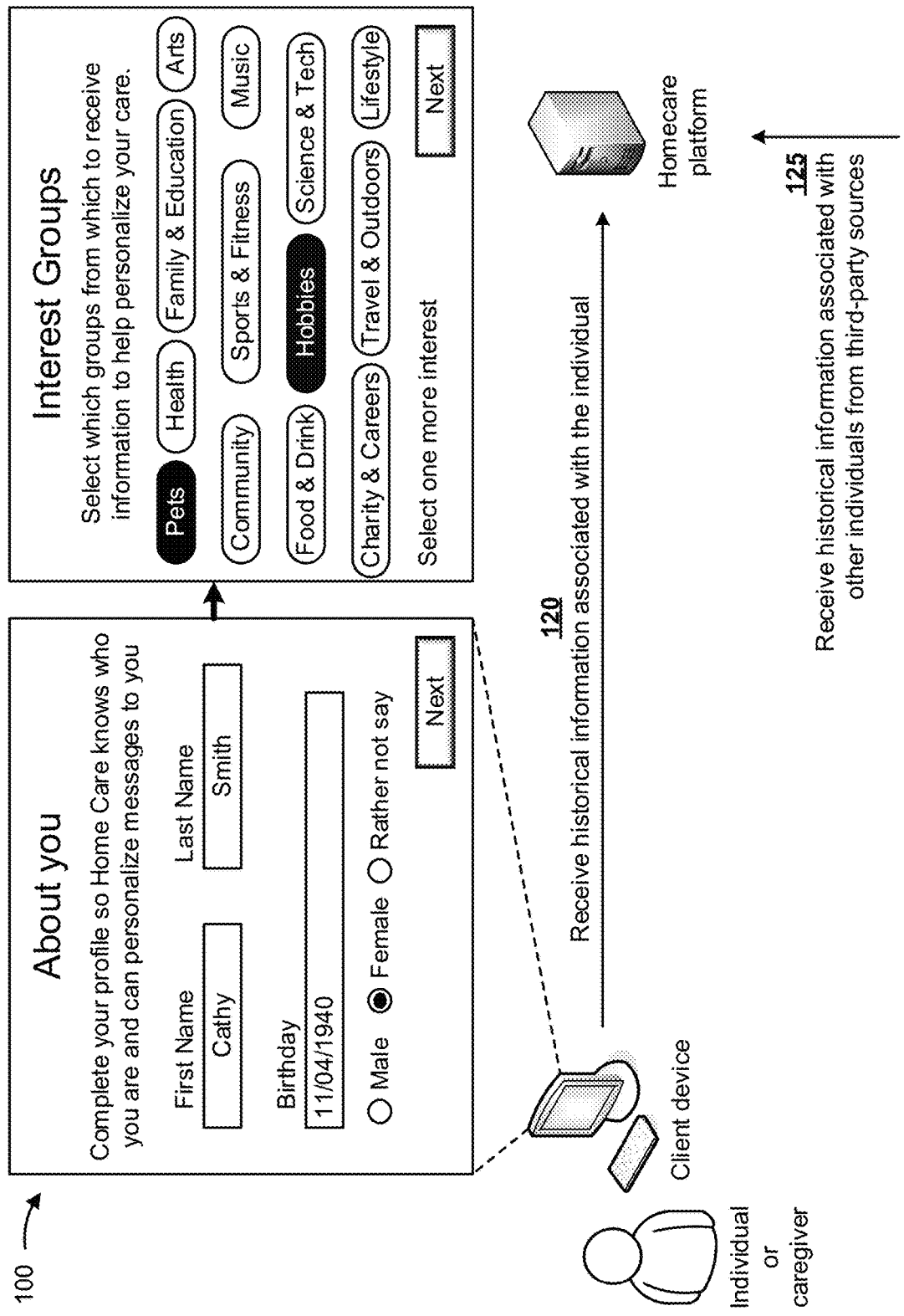

In some implementations, as shown in FIG. 1B, the homecare application may cause the client device to display a user interface for receiving historical information associated with the individual. In some implementations, the historical information associated with the individual may include information associated with a health history (e.g., mental issues, medical issues, required medications, and/or the like) of the individual, activities of the individual (e.g., wake up at a certain time, eat meals at certain times, take certain medications at certain times, and/or the like), and/or the like. In some implementations, the user interface may include information requesting a first name and a last name of the individual, a birthday of the individual, groups of interest to the individual (e.g., pets, health, family, education, arts, community, sports and fitness, music, food and drink, hobbies, science and technology, charity, careers, travel, outdoors, lifestyle, and/or the like), and/or the like. In some implementations, the historical information of the individual may be provided by a source other than the client device, such as a third-party data source that includes historical information associated with the individual.

As further shown in FIG. 1B, and by reference number 120, the homecare platform may receive, from the client device, the historical information associated with the individual. In some implementations, the homecare platform may store the historical information of the individual in a data structure (e.g., a database, a table, a list, and/or the like) associated with the homecare platform.

As further shown in FIG. 1B, and by reference number 125, the homecare platform may receive historical information associated with other individuals from third-party sources. In some implementations, the historical information associated with the other individuals may include information associated with health histories (e.g., mental issues, medical issues, required medications, and/or the like) of other individuals similar to the individual (e.g., similar ages, similar health histories, similar demographics, and/or the like), activities of the other individuals, and/or the like. In some implementations, the homecare platform may store the historical information of the other individuals in a data structure (e.g., a database, a table, a list, and/or the like) associated with the homecare platform.

In some implementations, if the homecare platform collects, stores, or employs personal information of individuals (e.g., the historical information described above), such information shall be used in accordance with laws concerning protection of personal information. Additionally, the collection, storage, and use of such information, by the homecare platform, may be subject to consent of the individual to such activity, for example, through well known "opt-in" or "opt-out" processes as can be appropriate for the situation and type of information. The homecare platform may store and use personal information in an appropriately secure manner reflective of the type of information (e.g., via encryption and anonymization techniques).

Figure 1C:
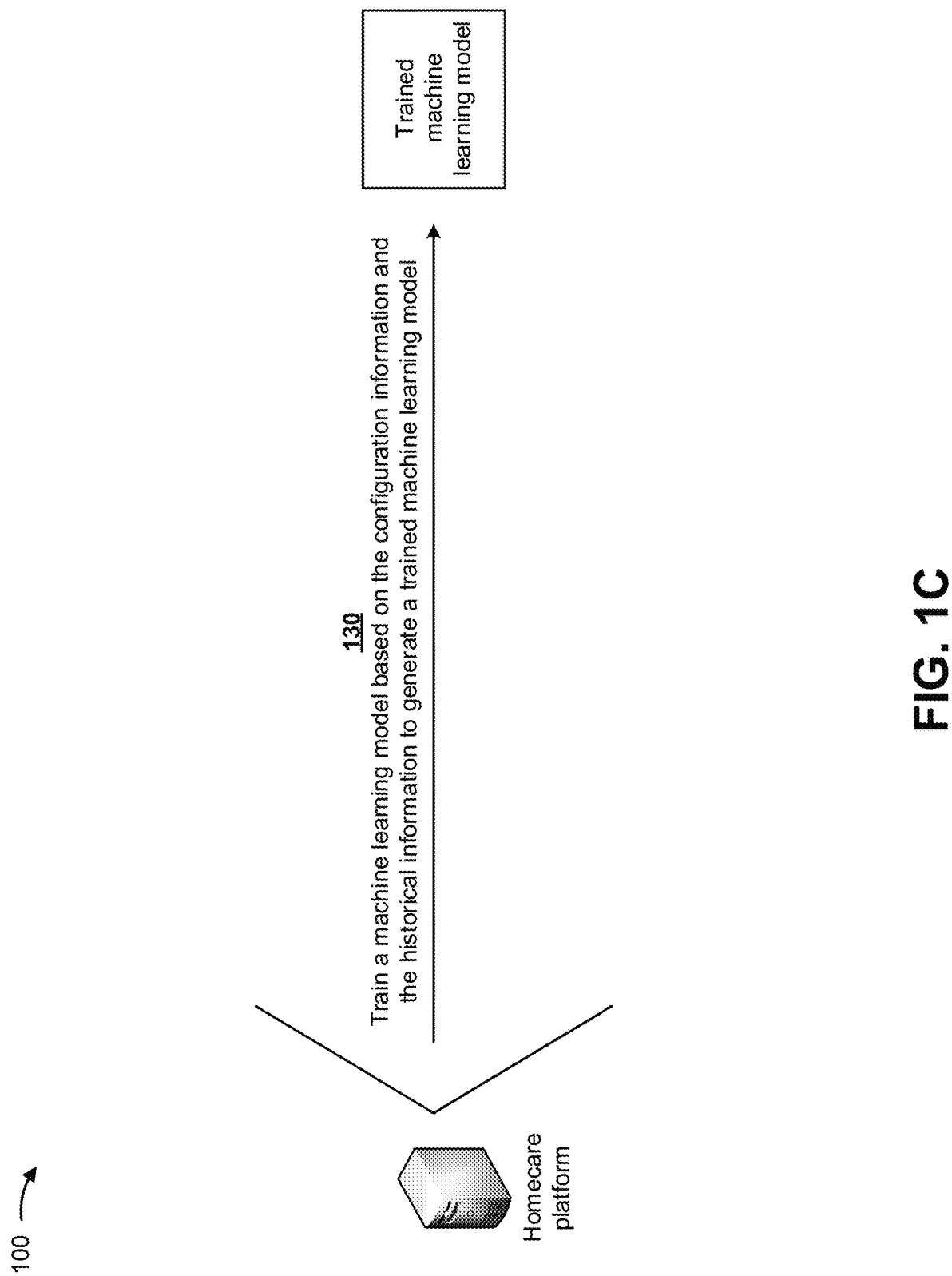

As shown in FIG. 1C, and by reference number 130, the homecare platform may train a machine learning model, based on the configuration information, the historical information of the individual, and the historical information of the other individuals, to generate a trained machine learning model. In some implementations, the machine learning model may include a neural network model, a deep learning model, a clustering model, a classification model, a numerical regression model, and/or the like.

In some implementations, the homecare platform may perform a training operation on the machine learning model with configuration and historical information (e.g., the configuration information, the historical information of the individual, and the historical information of the other individuals). For example, the homecare platform may separate the configuration and historical information into a training set, a validation set, a test set, and/or the like. In some implementations, the homecare platform may train the machine learning model using, for example, an unsupervised training procedure and based on the training set of the configuration and historical information. For example, the homecare platform may perform dimensionality reduction to reduce the configuration and historical information to a minimum feature set, thereby reducing resources (e.g., processing resources, memory resources, and/or the like) to train the machine learning model, and may apply a classification technique, to the minimum feature set.

In some implementations, the homecare platform may use a logistic regression classification technique to determine a categorical outcome (e.g., that the configuration and historical information indicates that the individual performs particular activities). Additionally, or alternatively, the homecare platform may use a naïve Bayesian classifier technique. In this case, the homecare platform may perform binary recursive partitioning to split the configuration and historical information into partitions and/or branches, and use the partitions and/or branches to perform predictions (e.g., that the configuration and historical information indicates that the individual performs particular activities). Based on using recursive partitioning, the homecare platform may reduce utilization of computing resources relative to manual, linear sorting and analysis of data points, thereby enabling use of thousands, millions, or billions of data points to train the machine learning model, which may result in a more accurate model than using fewer data points.

Additionally, or alternatively, the homecare platform may use a support vector machine (SVM) classifier technique to generate a non-linear boundary between data points in the training set. In this case, the non-linear boundary is used to classify test data into a particular class.

Additionally, or alternatively, the homecare platform may train the machine learning model using a supervised training procedure that includes receiving input to the machine learning model from a subject matter expert, which may reduce an amount of time, an amount of processing resources, and/or the like to train the machine learning model of activity automatability relative to an unsupervised training procedure. In some implementations, the homecare platform may use one or more other model training techniques, such as a neural network technique, a latent semantic indexing technique, and/or the like. For example, the homecare platform may perform an artificial neural network processing technique (e.g., using a two-layer feedforward neural network architecture, a three-layer feedforward neural network architecture, and/or the like) to perform pattern recognition with regard to particular tasks indicated in the configuration and historical information. In this case, using the artificial neural network processing technique may improve an accuracy of the trained machine learning model generated by the homecare platform by being more robust to noisy, imprecise, or incomplete data, and by enabling the homecare platform to detect patterns and/or trends undetectable to human analysts or systems using less complex techniques.

Figure 1D:
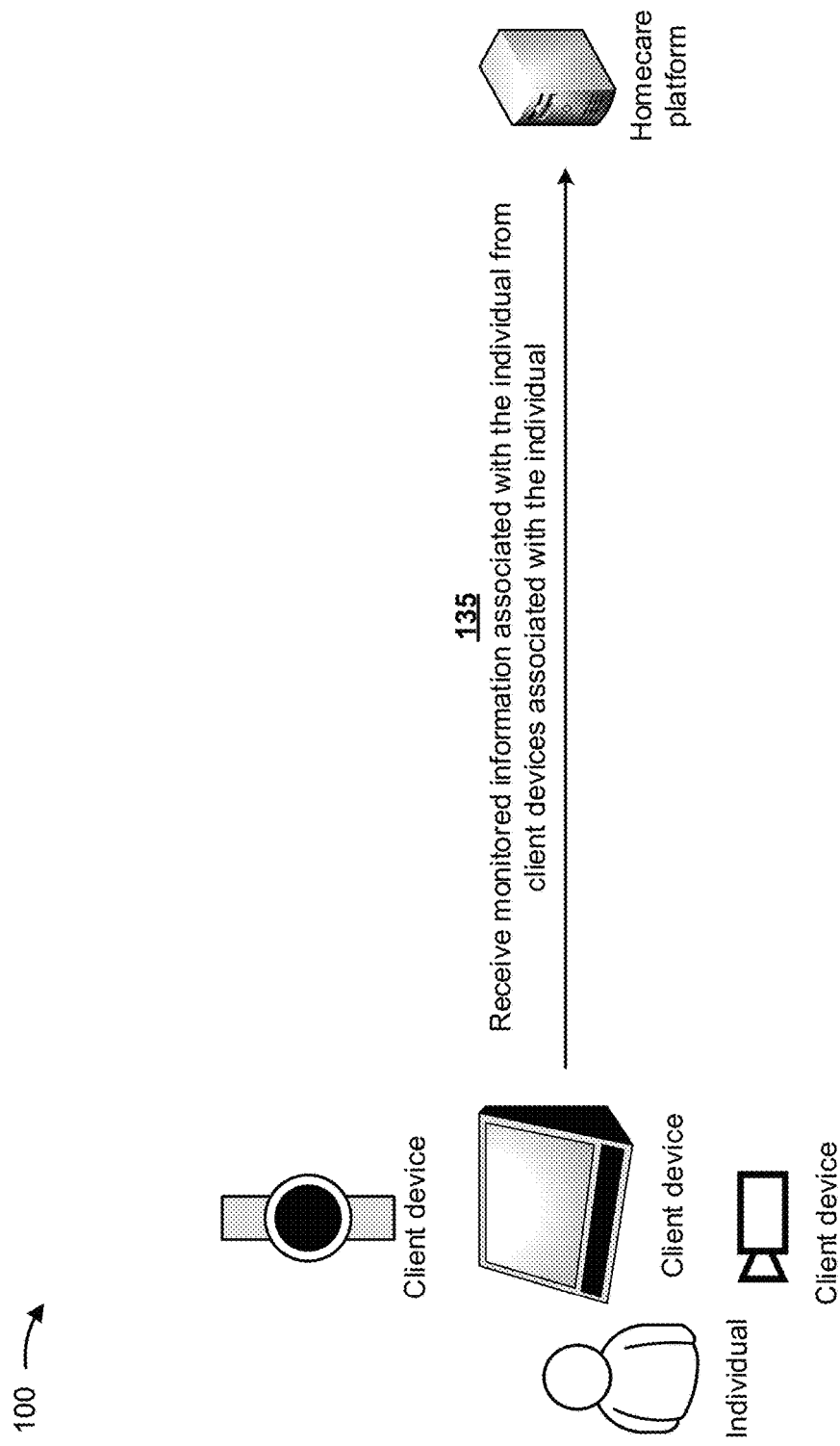

As shown in FIG. 1D, the individual may be associated with one or more client devices that may be used to monitor activities of the individual. For example, the one or more client devices may include a wearable device to monitor a heart rate, a number of steps taken, blood pressure, and/or the like of the individual; a wireless speaker and voice command device with an integrated virtual assistant (e.g., artificial intelligence) that offers interactive actions and handsfree activation; an image sensor to capture video and/or images of the individual; an audio sensor to capture audio of the individual; a laptop computer; a desktop computer; a tablet computer; a smartphone; and/or the like.

As further shown in FIG. 1D, and by reference number 135, the homecare platform may receive monitored information associated with the individual from the one or more client devices associated with the individual. In some implementations, the one or more client devices may provide a combination of voice-activated command, sound, video, tactile touch screen, Internet of Things (IoT), and/or the like so that the monitored information may be captured. In some implementations, the combination of voice-activated command, sound, video, tactile touch screen, IoT, and/or the like may utilize and/or stimulate a number of senses of the individual and may be utilized with behavioral analytics to provide information indicating a health of the individual. In some implementations, the monitored information may include video and/or images of the individual captured by an image sensor, audio of the individual captured by an audio sensor (e.g., a microphone, a motion detector, and/or the like), activity of the individual captured by a wearable device, a voice-command device, and/or the like, information associated with interactions of the individual with the client device, information associated with applications of the client device utilized by the individual, and/or the like.

In some implementations, the homecare platform may pre-process the monitored information so that the monitored information is provided in a common format that may be understood by the homecare platform. For example, the homecare platform may perform natural language processing (e.g., syntax, semantics, discourse, speech, and/or the like) on the monitored information so that the monitored information is readily understood by the homecare platform. In another example, the homecare platform may perform video analytics on the video of the individual in order to interpret the video (e.g., determine whether the individual took medicine, is standing up, is sitting down, and/or the like). In another example, the homecare platform may perform voice or audio recognition on the audio of the individual in order to interpret the audio (e.g., determine whether the individual is having trouble breathing, seems depressed, is in trouble, and/or the like).

Figure 1E:
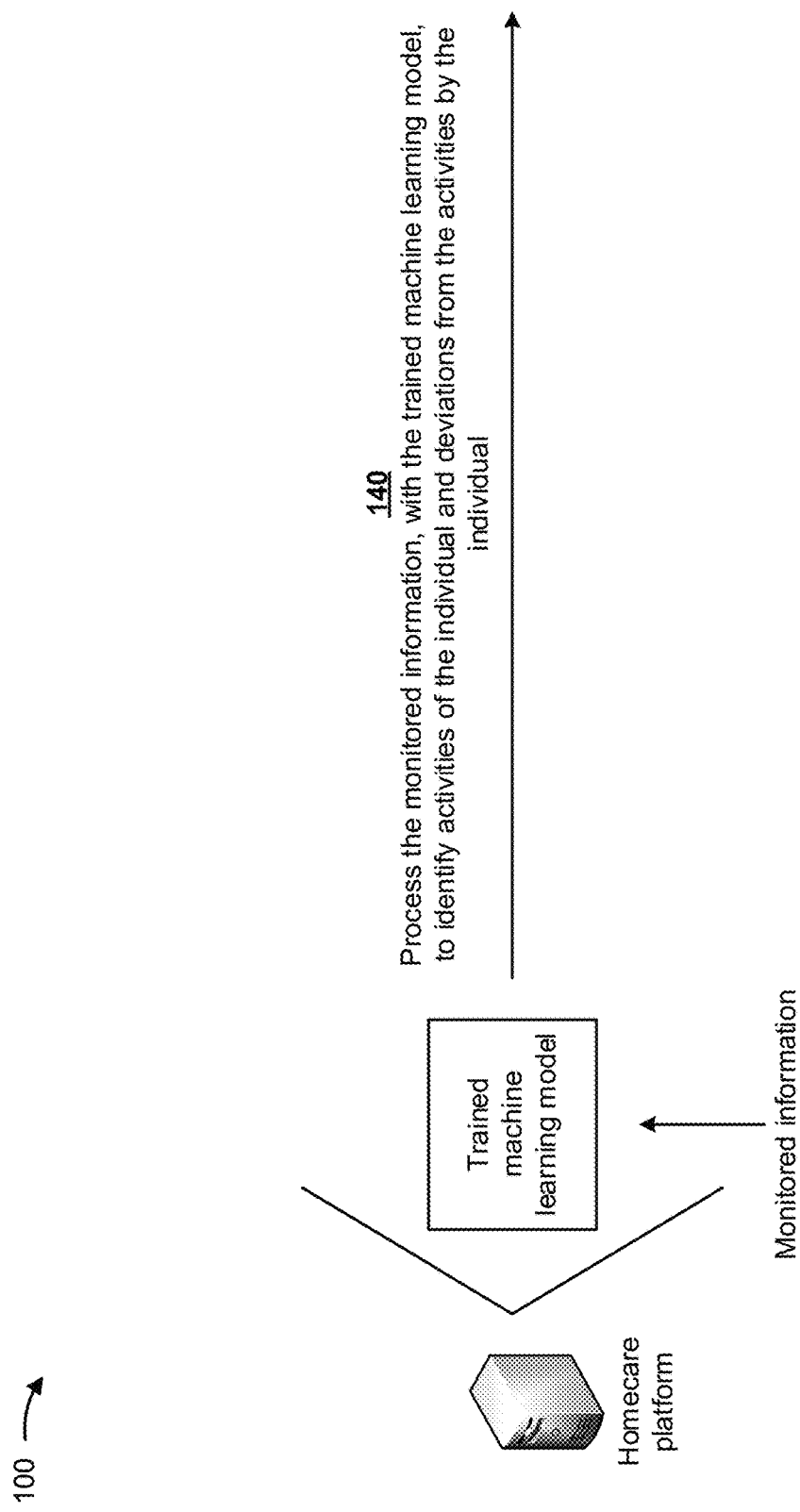

As shown in FIG. 1E, and by reference number 140, the homecare platform may process the monitored information, with the trained machine learning model, to identify activities of the individual and deviations from the activities by the individual. In some implementations, the homecare platform may utilize the identified activities to determine a routine associated with the individual (e.g., a time the individual wakes up, a time the individual goes to sleep, a time associated with when the individual exercises, and/or the like).

In some implementations, the machine learning model may include complex models that analyze a massive amount of data (i.e., an amount of data that cannot be processed objectively by a human actor), recognize patterns among the data, and make a prediction without requiring a person to program specific instructions. In some implementations, information associated with the activities of the individual may include a daily score associated with a mental capacity (e.g., a mind score) of the individual, a daily score associated with a physical capacity (e.g., a body score) of the individual, a daily score associated with home safety (e.g., a home score) of the individual, applications of the client device utilized by the individual, and/or the like. In some implementations, information associated with the deviations from the activities by the individual may include information associated with changes in the mind score, the body score, or the home score, the individual not taking medications, the individual not properly exercising, the individual not interacting with other people, the individual not eating, the individual not bathing, and/or the like.

In some implementations, the homecare platform may provide information associated with the activities and the deviations from the activities to a storage device, for display to the client device associated with the caregiver, to the client device associated with the individual, to a client device associated with a support user, and/or the like. In some implementations, the support user may include emergency services personnel (e.g., associated with a fire department, a police department, an emergency service system, and/or the like), a doctor, a nurse, a relative, and/or the like. If the individual is experiencing an emergency, a physical health issue, a mental health issue, and/or the like, the homecare platform may notify the support user and the support user may perform an action (e.g., dispatch an ambulance, call the caregiver, dispatch a police officer, dispatch a fire truck, and/or the like) based on being notified.

In some implementations, the homecare platform may have access to third-party application program interfaces (APIs) that provide services to the individual. For example, the third-party APIs may provide a video call service so that the individual can make video calls, a music service so that the individual can listen to music, a news service that provides news to the individual, a messaging service so the individual can send voice and text messages, a health appointments service to manage doctor and dentist appointments for the individual, a medicine reminders service to schedule medicine reminders for the individual, an activity service (e.g., that interacts with a wearable device) to track the physical activity of the individual, a home services service that schedules home services (e.g., gardening, cleaning, etc.) for the individual, a home security service that provides a security system for the home of the individual, a grocery shopping service that manages orders and deliveries of groceries to the individual, an events service that provides updates on local events to the individual, a banking service that manages bills and finances of the individual, and/or the like. In this way, the homecare platform may facilitate access of the individual to an ecosystem of partners or services (e.g., remote personal banking, grocery shopping, virtual health consultation, and/or the like). In some implementations, the homecare platform may provide a clinician portal for various healthcare providers (e.g., doctors, nurses, psychologists, and/or the like) so that such providers can provide an integrated care plan, visit reminders, visit notes, and/or the like to the individual.

Figure 1F:
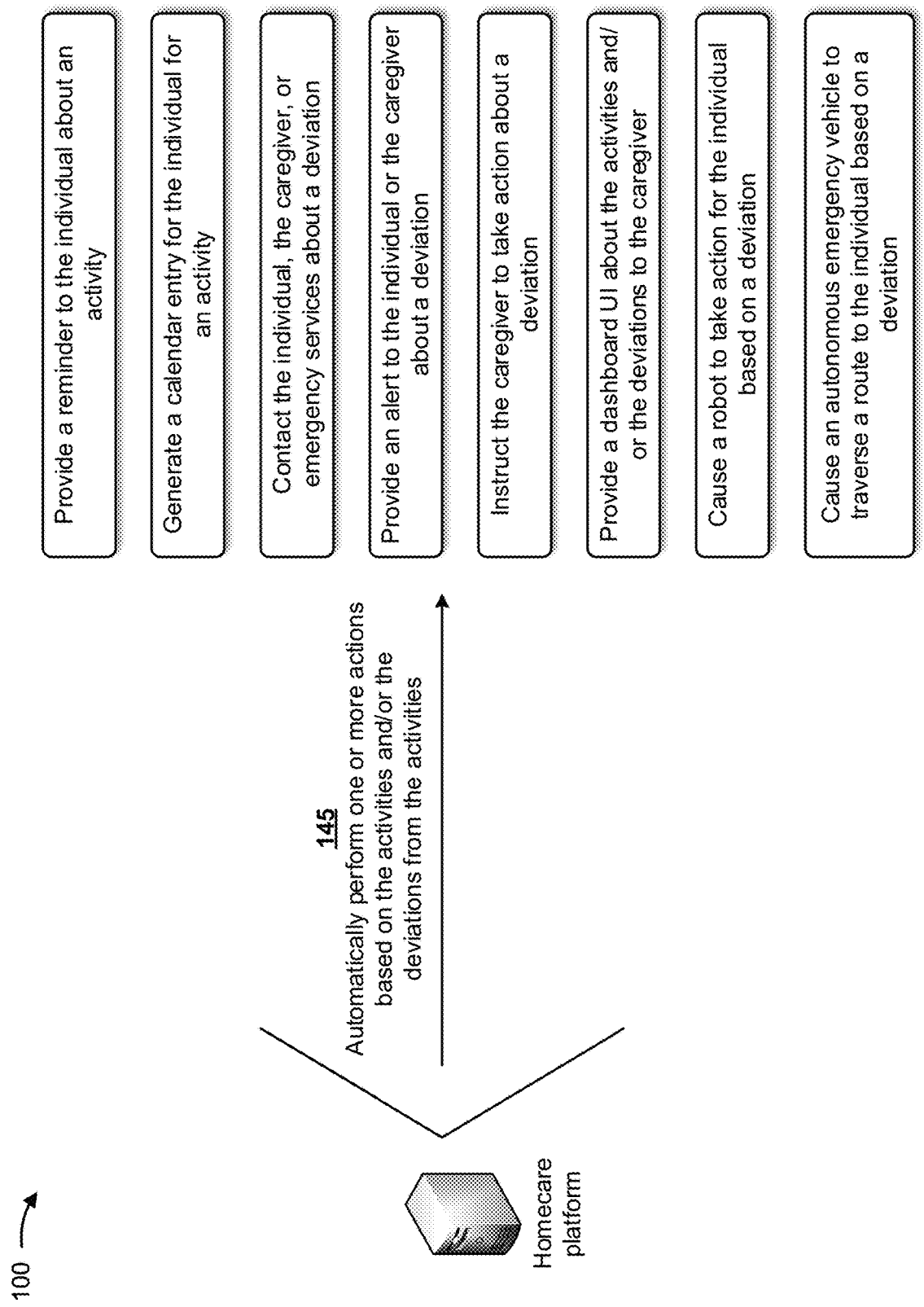

As shown in FIG. 1F, and by reference number 145, the homecare platform may automatically perform one or more actions based on the activities of the individual and/or the deviations from the activities of the individual. In some implementations, the one or more actions may include providing a reminder (e.g., via an email, a telephone call, a text message, and/or the like) to the client device of the individual about an activity. For example, the homecare platform may remind the individual that an aerobics class is on television at a particular time. In this way, the homecare platform may provide reminders to individuals who may have memory loss.

In some implementations, the one or more actions may include generating a calendar entry (e.g., for a calendar of the individual) for the client device of the individual about an activity. For example, the homecare platform may add a calendar entry indicating that the individual has a doctor's appointment on a certain day. In this way, the homecare platform may ensure that individuals perform activities at appropriate times.

In some implementations, the one or more actions may include contacting the client devices of the individual, the caregiver, and/or emergency services about a deviation. For example, the homecare platform may contact (e.g., via an email, a telephone call, a text message, and/or the like) the individual, the caregiver, and/or emergency services (e.g., a paramedic) if the deviation indicates that the individual may be having a heart attack. In this way, the homecare platform may ensure that individuals are tended to quickly in the event of an emergency, which may save lives.

In some implementations, the one or more actions may include providing an alert to the client devices of the individual and/or the caregiver about a deviation. For example, the homecare platform may provide an alert (e.g., via an email, a telephone call, a text message, and/or the like) to the individual and/or the caregiver if the deviation indicates that the individual did not eat breakfast. In this way, the homecare platform may ensure that individuals perform necessary activities to maintain a healthy lifestyle.

In some implementations, the one or more actions may include instructing the caregiver (e.g., via the client device) to take action about a deviation. For example, the homecare platform may provide instructions (e.g., via an email, a telephone call, a text message, and/or the like) instructing the caregiver to immediately travel to the individual's home if the individual fell down. In this way, the homecare platform may ensure that individuals are tended to quickly in the event of an accident.

In some implementations, the one or more actions may include providing a dashboard user interface (UI) about the activities and/or the deviations to the client devices of the individual and/or the caregiver. For example, the homecare platform may provide a dashboard user interface indicating a daily score associated with a mental capacity (e.g., a mind score) of the individual, a daily score associated with a physical capacity (e.g., a body score) of the individual, a daily score associated with home safety (e.g., a home score) of the individual, applications of the client device utilized by the individual, and/or the like. In this way, the homecare platform may enable the individual and/or the caregiver to track the individual's health on a daily basis.

In some implementations, the one or more actions may include causing a robot to take action for the individual based on a deviation. For example, the homecare platform may cause a robot to provide medication to the individual if the individual is unable to walk due to an accident. In this way, the homecare platform may ensure that individuals are tended to quickly in the event of an accident.

In some implementations, the one or more actions may include causing an autonomous emergency vehicle to traverse a route to the individual based on a deviation. For example, the homecare platform may cause an autonomous emergency vehicle to travel to the individual's home if the deviation indicates that the individual may be having a stroke. In this way, the homecare platform may ensure that individuals are tended to quickly in the event of an emergency, which may save lives.

Figure 1G:
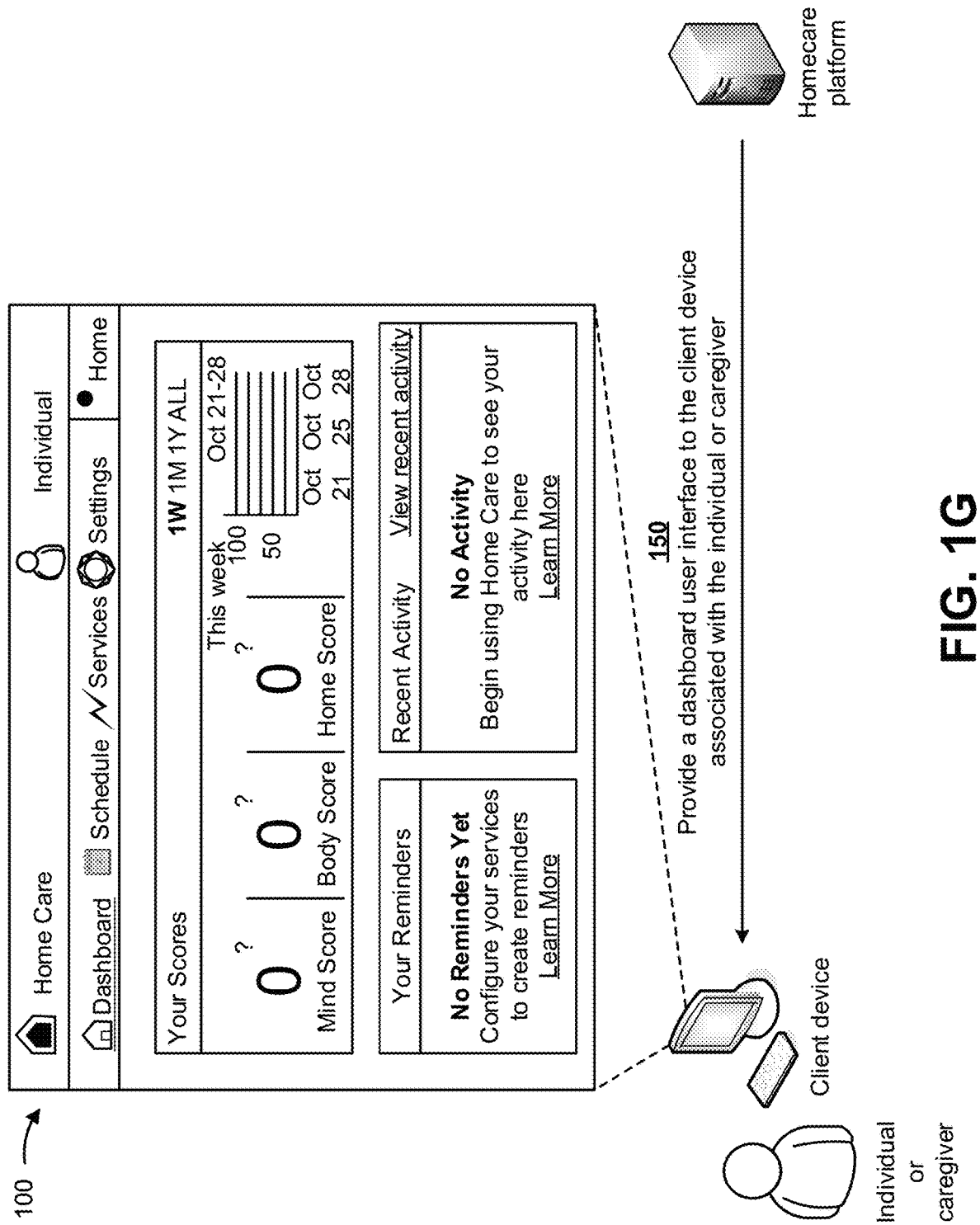

As shown in FIG. 1G, and by reference number 150, the homecare platform may provide a dashboard user interface to the client device associated with the individual and/or the caregiver. In some implementations, the client device may receive dashboard user interface and may display the dashboard user interface to the individual and/or the caregiver. In some implementations, the dashboard user interface may include information associated with a schedule of the individual, services provided to the individual (e.g., via the third-party APIs), the mind score of the individual, the body score of the individual, the home score associated with the individual, reminders for the individual, recent activity of the individual, and/or the like.

In this way, several different stages of the process for identifying activities and deviations from the activities by an individual are automated via a machine learning model, which may remove human subjectivity and waste from the process, and which may improve speed and efficiency of the process and conserve computing resources (e.g., processing resources, memory resources, and/or the like). Furthermore, implementations described herein use a rigorous, computerized process to perform tasks or roles that were not previously performed or were previously performed using subjective human intuition or input. For example, currently there does not exist a technique that utilizes a machine learning model to identify activities and deviations from the activities by an individual. Finally, automating the process for identifying actions, and deviations from the activities by an individual, conserves computing resources (e.g., processing resources, memory resources, and/or the like) that would otherwise be wasted in attempting to identify activities and deviations from the activities by an individual.

As indicated above, FIGS. 1A-1G are provided merely as examples. Other examples may differ from what was described with regard to FIGS. 1A-1G.

Figure 2:
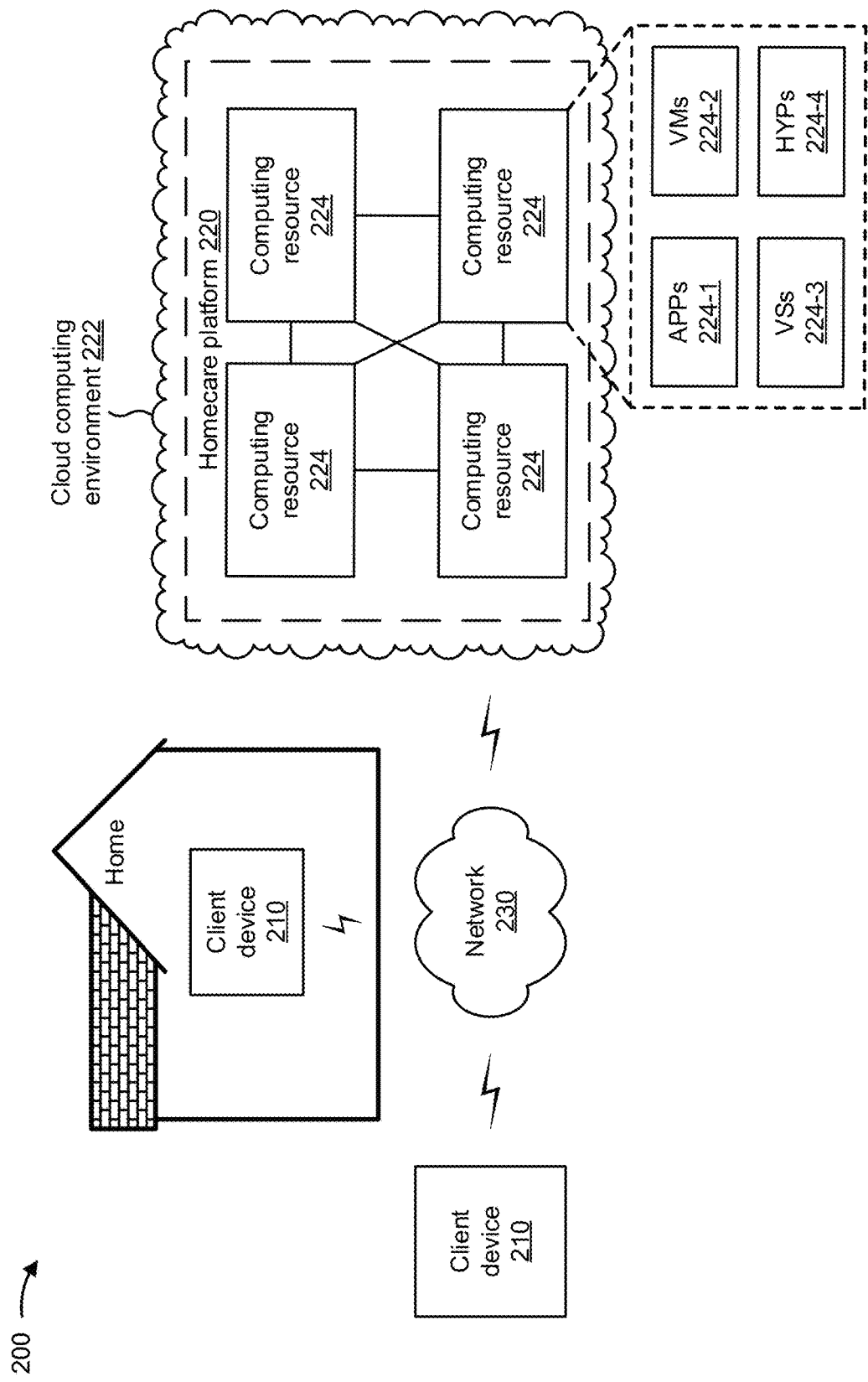
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a client device 210, a homecare platform 220, and a network 230. Devices of environment 200 may interconnect via wired connections, wireless connections, or a combination of wired and wireless connections.

Client device 210 includes one or more devices capable of receiving, generating, storing, processing, and/or providing information, such as information described herein. For example, client device 210 may include a mobile phone (e.g., a smart phone, a radiotelephone, etc.), a laptop computer, a tablet computer, a desktop computer, a handheld computer, a gaming device, a wearable communication device (e.g., a smart watch, a pair of smart glasses, a heart rate monitor, a fitness tracker, smart clothing, smart jewelry, a head mounted display, etc.), or a similar type of device. In some implementations, client device 210 may receive information from and/or transmit information to homecare platform 220.

Homecare platform 220 includes one or more devices that utilize a machine learning model to identify activities and deviations from the activities by an individual. In some implementations, homecare platform 220 may be designed to be modular such that certain software components may be swapped in or out depending on a particular need. As such, homecare platform 220 may be easily and/or quickly reconfigured for different uses. In some implementations, homecare platform 220 may receive information from and/or transmit information to one or more client devices 210.

In some implementations, as shown, homecare platform 220 may be hosted in a cloud computing environment 222. Notably, while implementations described herein describe homecare platform 220 as being hosted in cloud computing environment 222, in some implementations, homecare platform 220 may not be cloud-based (i.e., may be implemented outside of a cloud computing environment) or may be partially cloud-based.

Cloud computing environment 222 includes an environment that hosts homecare platform 220. Cloud computing environment 222 may provide computation, software, data access, storage, etc. services that do not require end-user knowledge of a physical location and configuration of system(s) and/or device(s) that hosts homecare platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host homecare platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by client device 210. Application 224-1 may eliminate a need to install and execute the software applications on client device 210. For example, application 224-1 may include software associated with homecare platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., a user of client device 210 or an operator of homecare platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
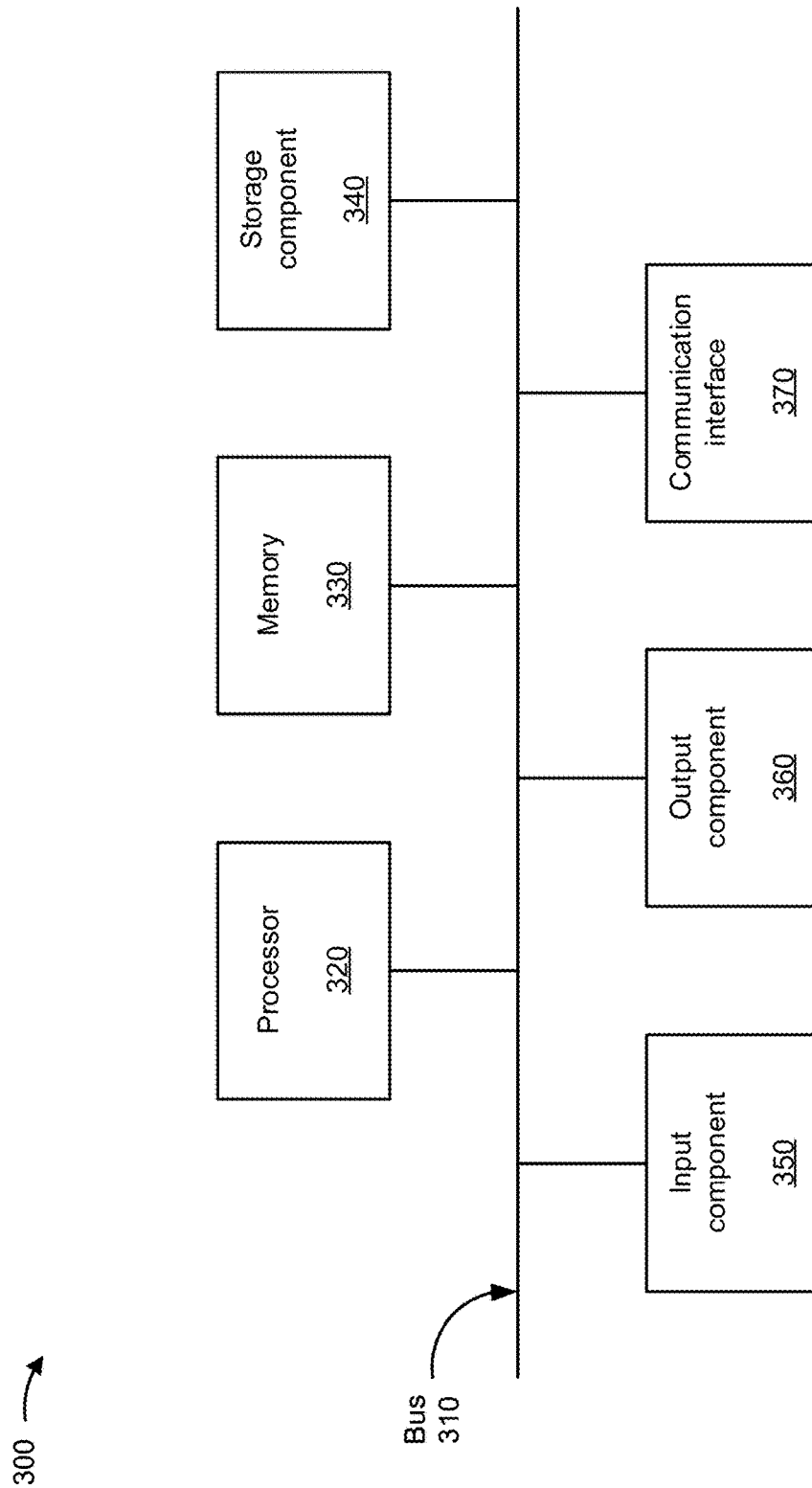
FIG. 3 is a diagram of example components of one or more devices of FIG. 2.

FIG. 3 is a diagram of example components of a device 300. Device 300 may correspond to client device 210, homecare platform 220, and/or computing resource 224. In some implementations, client device 210, homecare platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for utilizing a machine learning model to identify activities and deviations from the activities by an individual. In some implementations, one or more process blocks of FIG. 4 may be performed by a homecare platform (e.g., homecare platform 220). In some implementations, one or more process blocks of FIG. 4 may be performed by another device or a group of devices separate from or including the homecare platform, such as a client device (e.g., client device 210).

As shown in FIG. 4, process 400 may include receiving configuration information associated with configuring an application for monitoring an individual, wherein the configuration information includes at least one of information identifying physical characteristics of the individual, information identifying medications taken by the individual, personal information of the individual, or information associated with a caregiver of the individual (block 410). For example, the homecare platform (e.g., using computing resource 224, processor 320, communication interface 370, and/or the like) may receive configuration information associated with configuring an application for monitoring an individual, as described above in connection with FIGS. 1A-2. In some implementations, the configuration information may include at least one of information identifying physical characteristics of the individual, information identifying medications taken by the individual, personal information of the individual, or information associated with a caregiver of the individual.

As further shown in FIG. 4, process 400 may include receiving historical information associated with the individual, wherein the historical information includes at least one of information associated with a health history of the individual, information associated with health histories of other individuals, information associated with activities of the individual, or information associated with activities of the other individuals (block 420). For example, the homecare platform (e.g., using computing resource 224, processor 320, communication interface 370, and/or the like) may receive historical information associated with the individual, as described above in connection with FIGS. 1A-2. In some implementations, the historical information may include at least one of information associated with a health history of the individual, information associated with health histories of other individuals, information associated with activities of the individual, or information associated with activities of the other individuals.

As further shown in FIG. 4, process 400 may include training, based on the configuration information and the historical information, a machine learning model to generate a trained machine learning model (block 430). For example, the homecare platform (e.g., using computing resource 224, processor 320, storage component 340, and/or the like) may train, based on the configuration information and the historical information, a machine learning model to generate a trained machine learning model, as described above in connection with FIGS. 1A-2. In some implementations, the unit test may be performed on the new software code.

As further shown in FIG. 4, process 400 may include receiving, via the application, monitored information associated with the individual from one or more client devices associated with the individual (block 440). For example, the homecare platform (e.g., using computing resource 224, processor 320, communication interface 370, and/or the like) may receive, via the application, monitored information associated with the individual from one or more client devices associated with the individual, as described above in connection with FIGS. 1A-2.

As further shown in FIG. 4, process 400 may include processing the monitored information, with the trained machine learning model, to identify one or more activities of the individual and one or more deviations from the one or more activities by the individual (block 450). For example, the homecare platform (e.g., using computing resource 224, processor 320, memory 330, and/or the like) may process the monitored information, with the trained machine learning model, to identify one or more activities of the individual and one or more deviations from the one or more activities by the individual, as described above in connection with FIGS. 1A-2. In some implementations, the functional test may be performed on the new software code.

As further shown in FIG. 4, process 400 may include performing one or more actions based on the one or more activities of the individual and/or the one or more deviations from the one or more activities by the individual (block 460). For example, the homecare platform (e.g., using computing resource 224, processor 320, storage component 340, communication interface 370, and/or the like) may perform one or more actions based on the one or more activities of the individual and/or the one or more deviations from the one or more activities by the individual, as described above in connection with FIGS. 1A-2.

Process 400 may include additional implementations, such as any single implementation or any combination of implementations described below and/or described with regard to any other process described herein.

In some implementations, when performing the one or more actions, the homecare platform may provide a reminder, to a particular client device of the one or more client devices associated with the individual, about one of the one or more activities, may generate a calendar entry, to a particular client device of the one or more client devices associated with the individual, for one of the one or more activities, may contact the individual, the caregiver, or emergency services about one of the one or more deviations, may provide an alert, to the particular client device associated with the individual or to a client device associated with the caregiver, about one of the one or more deviations, may instruct the caregiver, via the client device associated with the caregiver, to take action for one of the one or more deviations, and/or may provide, to the client device associated with the caregiver, a user interface that includes information indicating the one or more activities and/or the one or more deviations.

In some implementations, when performing the one or more actions, the homecare platform may cause a robot to take action for the individual based on one of the one or more deviations, may cause the robot to take action for the individual based on one of the one or more activities, may cause an autonomous emergency vehicle to traverse a route to the individual based on one of the one or more deviations, and/or may cause an autonomous service vehicle to traverse a route to the individual based on one of the one or more activities.

In some implementations, the homecare platform may generate a mental capacity score for the individual based on the one or more activities of the individual and/or the one or more deviations from the one or more activities by the individual, may generate a physical capacity score for the individual based on the one or more activities of the individual and/or the one or more deviations from the one or more activities by the individual, and may generate an overall score for the individual based on the mental capacity score and the physical capacity score. In some implementations, the homecare platform may perform the one or more actions based on the overall score.

In some implementations, the monitoring information may include at least one of video of the individual captured by an image sensor associated with the individual, audio of the individual captured by an audio sensor associated with the individual, activity of the individual captured by a sensor associated with the individual, information associated with interactions of the individual with the one or more client devices, or information associated with applications of the one or more client devices utilized by the individual. In some implementations, the machine learning model may include one or more of a neural network model, a deep learning model, a clustering model, a classification model, or a numerical regression model.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIG. 5 is a flow chart of an example process 500 for utilizing a machine learning model to identify activities and deviations from the activities by an individual. In some implementations, one or more process blocks of FIG. 5 may be performed by a homecare platform (e.g., homecare platform 220). In some implementations, one or more process blocks of FIG. 5 may be performed by another device or a group of devices separate from or including the homecare platform, such as a client device (e.g., client device 210).

As shown in FIG. 5, process 500 may include receiving historical information associated with an individual to be monitored, wherein the historical information includes at least one of information associated with a health history of the individual, information associated with health histories of other individuals, information associated with activities of the individual, or information associated with activities of the other individuals (block 510). For example, the homecare platform (e.g., using computing resource 224, processor 320, communication interface 370, and/or the like) may receive historical information associated with an individual to be monitored, as described above in connection with FIGS. 1A-2. In some implementations, the historical information may include at least one of information associated with a health history of the individual, information associated with health histories of other individuals, information associated with activities of the individual, or information associated with activities of the other individuals.

As further shown in FIG. 5, process 500 may include receiving monitored information associated with the individual from one or more client devices associated with the individual (block 520). For example, the homecare platform (e.g., using computing resource 224, processor 320, communication interface 370, and/or the like) may receive monitored information associated with the individual from one or more client devices associated with the individual, as described above in connection with FIGS. 1A-2.

As further shown in FIG. 5, process 500 may include pre-processing the monitored information to generate pre-processed monitored information that is understood by a trained machine learning model (block 530). For example, the homecare platform (e.g., using computing resource 224, processor 320, memory 330, and/or the like) may pre-process the monitored information to generate pre-processed monitored information that is understood by the trained machine learning model, as described above in connection with FIGS. 1A-2.

As further shown in FIG. 5, process 500 may include processing the pre-processed monitored information, with the trained machine learning model, to identify one or more activities of the individual and one or more deviations from the one or more activities by the individual (block 540). For example, the homecare platform (e.g., using computing resource 224, processor 320, memory 330, storage component 340, and/or the like) may process the pre-processed monitored information, with a trained machine learning model, to identify one or more activities of the individual and one or more deviations from the one or more activities by the individual, as described above in connection with FIGS. 1A-2.

As further shown in FIG. 5, process 500 may include performing one or more actions based on the one or more activities of the individual and/or the one or more deviations from the one or more activities by the individual (block 550). For example, the homecare platform (e.g., using computing resource 224, processor 320, memory 330, communication interface 370, and/or the like) may perform one or more actions based on the one or more activities of the individual and/or the one or more deviations from the one or more activities by the individual, as described above in connection with FIGS. 1A-2.

Process 500 may include additional implementations, such as any single implementation or any combination of implementations described below and/or described with regard to any other process described herein.

In some implementations, when performing the one or more actions, the homecare platform may provide a reminder, to a particular client device of the one or more client devices associated with the individual, about one of the one or more activities, may generate a calendar entry, to a particular client device of the one or more client devices associated with the individual, for one of the one or more activities, may contact the individual, a caregiver, or emergency services about one of the one or more deviations, may provide an alert, to the particular client device associated with the individual or to a client device associated with the caregiver, about one of the one or more deviations, may instruct the caregiver, via the client device associated with the caregiver, to take action for one of the one or more deviations, may provide, to the client device associated with the caregiver, a user interface that includes information indicating the one or more activities and/or the one or more deviations, may cause a robot to take action for the individual based on one of the one or more deviations, may cause the robot to take action for the individual based on one of the one or more activities, may cause an autonomous emergency vehicle to traverse a route to the individual based on one of the one or more deviations, and/or may cause an autonomous service vehicle to traverse a route to the individual based on one of the one or more activities.

In some implementations, when pre-processing the monitored information, the homecare platform may perform natural language processing on textual information associated with the monitored information, may perform video analytics on video information associated with the monitored information, and/or may perform voice or audio recognition on audio information associated with the monitored information.

In some implementations, the homecare platform may generate a mental capacity score for the individual based on the one or more activities of the individual and/or the one or more deviations from the one or more activities by the individual, may generate a physical capacity score for the individual based on the one or more activities of the individual and/or the one or more deviations from the one or more activities by the individual, and may generate an overall score for the individual based on the mental capacity score and the physical capacity score. In some implementations, the homecare platform may perform the one or more actions based on the overall score.

In some implementations, the monitoring information may include at least one of video of the individual captured by an image sensor associated with the individual, audio of the individual captured by an audio sensor associated with the individual, activity of the individual captured by a sensor associated with the individual, information associated with interactions of the individual with the one or more client devices, or information associated with applications of the one or more client devices utilized by the individual.

In some implementations, the homecare platform may provide third-party application programming interfaces (APIs) to the one or more client devices associated with the individual, where the third-party APIs provide one or more of a video call service to enable the individual to make video calls, a music service to enable the individual to listen to music, a news service to provide news to the individual, a messaging service to enable the individual to send voice and text messages, a health appointments service to manage doctor and dentist appointments for the individual, a medicine reminders service to schedule medicine reminders for the individual, an activity service to track physical activity of the individual, a home services service to schedule home services for the individual, a home security service to provide a security system for the individual, a grocery shopping service to manage orders and deliveries of groceries to the individual, an events service to provide updates on local events to the individual, or a banking service to manage bills and finances of the individual.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

FIG. 6 is a flow chart of an example process 600 for utilizing a machine learning model to identify activities and deviations from the activities by an individual. In some implementations, one or more process blocks of FIG. 6 may be performed by a homecare platform (e.g., homecare platform 220). In some implementations, one or more process blocks of FIG. 6 may be performed by another device or a group of devices separate from or including the homecare platform, such as a client device (e.g., client device 210).

As shown in FIG. 6, process 600 may include providing an application for monitoring an individual to a client device associated with a caregiver of the individual (block 610). For example, the homecare platform (e.g., using computing resource 224, processor 320, communication interface 370, and/or the like) may provide an application for monitoring an individual to a client device associated with a caregiver of the individual, as described above in connection with FIGS. 1A-2.

As further shown in FIG. 6, process 600 may include receiving a machine learning model that has been trained based on configuration information and historical information, wherein the configuration information is associated with configuring the application and includes at least one of information identifying physical characteristics of the individual, information identifying medications taken by the individual, personal information of the individual, or information associated with the caregiver of the individual, and wherein the historical information includes at least one of information associated with a health history of the individual, information associated with health histories of other individuals, information associated activities of the individual, or information associated with activities of the other individuals (block 620). For example, the homecare platform (e.g., using computing resource 224, processor 320, communication interface 370, and/or the like) may receive a machine learning model that has been trained based on configuration information and historical information, as described above in connection with FIGS. 1A-2. In some implementations, the configuration information may be associated with configuring the application and may include at least one of information identifying physical characteristics of the individual, information identifying medications taken by the individual, personal information of the individual, or information associated with the caregiver of the individual. In some implementations, the historical information may include at least one of information associated with a health history of the individual, information associated with health histories of other individuals, information associated with activities of the individual, or information associated with activities of the other individuals.

As further shown in FIG. 6, process 600 may include providing third-party application programming interfaces (APIs) to one or more client devices associated with the individual (block 630). For example, the homecare platform (e.g., using computing resource 224, processor 320, storage component 340, communication interface 370, and/or the like) may provide third-party application programming interfaces (APIs) to one or more client devices associated with the individual, as described above in connection with FIGS. 1A-2.

As further shown in FIG. 6, process 600 may include receiving, via the application and the third-party APIs, monitored information associated with the individual from the client device associated with the caregiver and/or the one or more client devices associated with the individual (block 640). For example, the homecare platform (e.g., using computing resource 224, processor 320, memory 330, communication interface 370, and/or the like) may receive, via the application and the third-party APIs, monitored information associated with the individual from the client device associated with the caregiver and/or the one or more client devices associated with the individual, as described above in connection with FIGS. 1A-2.

As further shown in FIG. 6, process 600 may include processing the monitored information, with the machine learning model, to identify one or more activities of the individual and one or more deviations from the one or more activities by the individual (block 650). For example, the homecare platform (e.g., using computing resource 224, processor 320, memory 330, storage component 340, and/or the like) may process the monitored information, with the machine learning model, to identify one or more activities of the individual and one or more deviations from the one or more activities by the individual, as described above in connection with FIGS. 1A-2.

As further shown in FIG. 6, process 600 may include performing one or more actions based on the one or more activities of the individual and/or the one or more deviations from the one or more activities by the individual (block 660). For example, the homecare platform (e.g., using computing resource 224, processor 320, communication interface 370, and/or the like) may perform one or more actions based on the one or more activities of the individual and/or the one or more deviations from the one or more activities by the individual, as described above in connection with FIGS. 1A-2.

Process 600 may include additional implementations, such as any single implementation or any combination of implementations described below and/or described with regard to any other process described herein.

In some implementations, when performing the one or more actions, the homecare platform may provide a reminder, to a particular client device of the one or more client devices associated with the individual, about one of the one or more activities, to generate a calendar entry, to a particular client device of the one or more client devices associated with the individual, for one of the one or more activities, to contact the individual, the caregiver, or emergency services about one of the one or more deviations, to provide an alert, to the particular client device associated with the individual or to a client device associated with the caregiver, about one of the one or more deviations, to instruct the caregiver, via the client device associated with the caregiver, to take action for one of the one or more deviations, to provide, to the client device associated with the caregiver, a user interface that includes information indicating the one or more activities and/or the one or more deviations, to cause a robot to take action for the individual based on one of the one or more deviations, to cause the robot to take action for the individual based on one of the one or more activities, to cause an autonomous emergency vehicle to traverse a route to the individual based on one of the one or more deviations, and/or to cause an autonomous service vehicle to traverse a route to the individual based on one of the one or more activities.

In some implementations, the homecare platform may generate a mental capacity score for the individual based on the one or more activities of the individual and/or the one or more deviations from the one or more activities by the individual, may generate a physical capacity score for the individual based on the one or more activities of the individual and/or the one or more deviations from the one or more activities by the individual, may generate an overall score for the individual based on the mental capacity score and the physical capacity score, and may perform the one or more actions based on the overall score.

In some implementations, the monitoring information may include at least one of video of the individual captured by an image sensor associated with the individual, audio of the individual captured by an audio sensor associated with the individual, activity of the individual captured by a sensor associated with the individual, information associated with interactions of the individual with the one or more client devices, or information associated with applications of the one or more client devices utilized by the individual. In some implementations, the homecare platform may train the machine learning model based on the configuration information and the historical information.

In some implementations, the third-party APIs may provide one or more of a video call service to enable the individual to make video calls, a music service to enable the individual to listen to music, a news service to provide news to the individual, a messaging service to enable the individual to send voice and text messages, a health appointments service to manage doctor and dentist appointments for the individual, a medicine reminders service to schedule medicine reminders for the individual, an activity service to track physical activity of the individual, a home services service to schedule home services for the individual, a home security service to provide a security system for the individual, a grocery shopping service to manage orders and deliveries of groceries to the individual, an events service to provide updates on local events to the individual, or a banking service to manage bills and finances of the individual.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
receiving, by a device, configuration information associated with configuring an application for monitoring an individual,
wherein the configuration information includes at least one of:
information identifying physical characteristics of the individual,
information identifying medications taken by the individual,
personal information of the individual, or
information associated with a caregiver of the individual;
receiving, by the device, historical information associated with the individual,
wherein the historical information includes at least one of:
information associated with a health history of the individual,
information associated with health histories of other individuals,
information associated with activities of the individual, or
information associated with activities of the other individuals;
creating, by the device, a training set using the configuration information and the historical information;
training, by the device and using the training set, a machine learning model to generate a trained machine learning model;
providing, by the device, third-party application programming interfaces (APIs) to a plurality of client devices associated with the individual,
at least one of the third-party APIs enabling an activity service to track physical activity of the individual;
receiving, by the device and via the third party APIs, monitored information associated with the individual from the plurality of client devices,
the plurality of client devices including:
a wearable device,
an image sensor, and
an audio sensor, and
the monitored information including:
video captured by the image sensor,
audio captured by the audio sensor,
health information obtained by the wearable device, and
physical activity information obtained by the wearable device;
processing, by the device, the monitored information, with the trained machine learning model, to identify one or more activities of the individual;
determining, by the device, a routine associated with the individual based on identifying the one or more activities of the individual;
processing, by the device, the monitored information, with the trained machine learning model, to identify one or more deviations from the routine by the individual; and
performing, by the device, one or more actions based on identifying the one or more deviations,
the one or more actions including one or more of:
causing a robot to provide medication to the individual based on a first deviation of the one or more deviations, or
causing an autonomous emergency vehicle to traverse a route to the individual based on a second deviation of the one or more deviations.

2. The method of claim 1, wherein performing the one or more actions further comprises one or more of:

providing a reminder, to a particular client device of the plurality of client devices, about one of the one or more first activities;
generating a calendar entry, for the particular client device, regarding one of the one or more activities;
contacting the individual, the caregiver, or emergency services about one of the one or more deviations;
providing an alert, to the particular client device or to a client device associated with the caregiver, about one of the one or more deviations;
instructing the caregiver, via the client device associated with the caregiver, to take action for one of the one or more deviations; or
providing, to the client device associated with the caregiver, a user interface that includes information indicating the one or more activities and/or the one or more deviations.

3. The method of claim 1, wherein performing the one or more actions further comprises one or more of:
causing the robot to take action for the individual based on one of the one or more activities; or
causing an autonomous service vehicle to traverse a route to the individual based on one of the one or more activities.

4. The method of claim 1, further comprising:
generating a mental capacity score for the individual based on the one or more activities and/or the one or more deviations;
generating a physical capacity score for the individual based on the one or more activities and/or the one or more deviations; and
generating an overall score for the individual based on the mental capacity score and the physical capacity score.

5. The method of claim 4, where performing the one or more actions comprises:
performing the one or more actions based on the overall score.

6. The method of claim 1, wherein the monitored information includes at least one of:
information associated with interactions of the individual with the plurality of client devices, or
information associated with applications of the plurality of client devices utilized by the individual.

7. The method of claim 1, wherein the machine learning model includes one or more of:
a neural network model,
a deep learning model,
a clustering model,
a classification model, or
a numerical regression model.

8. A device, comprising:
one or more memories; and
one or more processors, communicatively coupled to the one or more memories, to:
receive historical information associated with an individual to be monitored,
wherein the historical information includes at least one of:
information associated with a health history of the individual,
information associated with health histories of other individuals,
information associated with activities of the individual, or
information associated with activities of the other individuals;
create a training set using the historical information;
provide third-party application programming interfaces (APIs) to a plurality of client devices associated with the individual,
at least one of the third-party APIs enabling an activity service to track physical activity of the individual;
receive, via the third-party APIs, monitored information associated with the individual from the plurality of client devices,
the plurality of client devices including:
a wearable device,
an image sensor, and
an audio sensor, and
the monitored information including:
video captured by the image sensor,
audio captured by the audio sensor,
health information obtained by the wearable device, and
physical activity information obtained by the wearable device;
pre-process the monitored information to generate pre-processed monitored information that is understood by a trained machine learning model;
process the pre-processed monitored information, with the trained machine learning model, to identify one or more activities of the individual;
determine a routine associated with the individual based on identifying the one or more activities of the individual;
process the pre-processed monitored information with the trained machine learning model to identify one or more deviations from the routine by the individual; and
perform one or more actions based on the one or more deviations from the routine by the individual,
the one or more actions including one or more of:
causing a robot to provide medication to the individual based on a first deviation of the one or more deviations, or
causing an autonomous emergency vehicle to traverse a route to the individual based on a second deviation of the one or more deviations.

9. The device of claim 8, wherein the one or more processors, when performing the one or more actions, are further to one or more of:
provide a reminder, to a particular client device of the plurality of client devices, about one of the one or more activities;
generate a calendar entry, for the particular client device, regarding one of the one or more activities;
contact the individual, a caregiver, or emergency services about one of the one or more deviations;
provide an alert, to the particular client device or to a client device associated with the caregiver, about one of the one or more deviations;
instruct the caregiver, via the client device associated with the caregiver, to take action for one of the one or more deviations;
provide, to the client device associated with the caregiver, a user interface that includes information indicating the one or more activities and/or the one or more deviations;
cause the robot to take action for the individual based on one of the one or more activities; or
cause an autonomous service vehicle to traverse a route to the individual based on one of the one or more activities.

10. The device of claim 8, wherein the one or more processors, when pre-processing the monitored information, are to one or more of:
perform natural language processing on textual information associated with the monitored information;
perform video analytics on video information associated with the monitored information; or
perform voice recognition or audio recognition on audio information associated with the monitored information.

11. The device of claim 8, wherein the one or more processors are further to:
generate a mental capacity score for the individual based on the one or more activities and/or the one or more deviations;
generate a physical capacity score for the individual based on the one or more activities and/or the one or more deviations; and
generate an overall score for the individual based on the mental capacity score and the physical capacity score.

12. The device of claim 11, wherein the one or more processors, when performing the one or more actions, are further to:
perform the one or more actions based on the overall score.

13. The device of claim 8, wherein the monitored information includes at least one of:
information associated with interactions of the individual with the plurality of client devices, or
information associated with applications of the plurality of client devices utilized by the individual.

14. The device of claim 8, wherein the third-party APIs provide one or more of:
a video call service to enable the individual to make video calls,
a music service to enable the individual to listen to music,
a news service to provide news to the individual,
a messaging service to enable the individual to send voice and text messages,
a health appointments service to manage doctor and dentist appointments for the individual,
a medicine reminders service to schedule medicine reminders for the individual,
a home services service to schedule home services for the individual,
a home security service to provide a security system for the individual,
a grocery shopping service to manage orders and deliveries of groceries to the individual,
an events service to provide updates on local events to the individual, or
a banking service to manage bills and finances of the individual.

15. A non-transitory computer-readable medium storing instructions, the instructions comprising:
one or more instructions that, when executed by one or more processors of a device, cause the one or more processors to:
provide an application for monitoring an individual to a client device associated with a caregiver of the individual;
receive a machine learning model that has been trained using a training set created using configuration information and historical information,
wherein the configuration information is associated with configuring the application and includes at least one of:
information identifying physical characteristics of the individual,
information identifying medications taken by the individual,
personal information of the individual, or
information associated with the caregiver; and
wherein the historical information includes at least one of:
information associated with a health history of the individual,
information associated with health histories of other individuals,
information associated with activities of the individual, or
information associated with activities of the other individuals;
provide third-party application programming interfaces (APIs) to a plurality of client devices associated with the individual,
at least one of the third-party APIs enabling an activity service to track physical activity of the individual;
receive, via the application and the third-party APIs, monitored information associated with the individual from the plurality of client devices,
the plurality of client devices including:
a wearable device,
an image sensor, and
an audio sensor, and
the monitored information including:
video captured by the image sensor,
audio captured by the audio sensor,
health information obtained by the wearable device, and
physical activity information obtained by the wearable device;
process the monitored information, with the machine learning model, to identify one or more activities of the individual;
determine a routine associated with the individual based on identifying the one or more activities of the individual;
process the monitored information, with the machine learning model, to identify one or more deviations from the routine by the individual; and
perform one or more actions based on the one or more deviations,
the one or more actions including one or more of:
causing a robot to provide medication to the individual based on a first deviation of the one or more deviations, or
causing an autonomous emergency vehicle to traverse a route to the individual based on a second deviation of the one or more deviations.

16. The non-transitory computer-readable medium of claim 15, wherein the one or more instructions, that cause the one or more processors to perform the one or more actions, further cause the one or more processors to one or more of:
provide a reminder, to a particular client device of the plurality of client devices, about one of the one or more activities;
generate a calendar entry, for the particular client device, regarding one of the one or more activities;
contact the individual, the caregiver, or emergency services about one of the one or more deviations;

provide an alert, to the particular client device or to the client device associated with the caregiver, about one of the one or more deviations;

instruct the caregiver, via the client device associated with the caregiver, to take action for one of the one or more deviations;

provide, to the client device associated with the caregiver, a user interface that includes information indicating the one or more activities and/or the one or more deviations;

cause the robot to take action for the individual based on one of the one or more activities;

cause an autonomous service vehicle to traverse a route to the individual based on one of the one or more activities.

17. The non-transitory computer-readable medium of claim 15, wherein the instructions further comprise:
one or more instructions that, when executed by the one or more processors, cause the one or more processors to:
generate a mental capacity score for the individual based on the one or more activities and/or the one or more deviations;
generate a physical capacity score for the individual based on the one or more activities and/or the one or more deviations; and
generate an overall score for the individual based on the mental capacity score and the physical capacity score; and
wherein the one or more instructions, that cause the one or more processors to perform the one or more actions, cause the one or more processors:
perform the one or more actions based on the overall score.

18. The non-transitory computer-readable medium of claim 15, wherein the monitored information includes at least one of:
information associated with interactions of the individual with the plurality of client devices, or
information associated with applications of the plurality of client devices utilized by the individual.

19. The non-transitory computer-readable medium of claim 15, wherein the third-party APIs provide one or more of:
a video call service to enable the individual to make video calls,
a music service to enable the individual to listen to music,
a news service to provide news to the individual,
a messaging service to enable the individual to send voice and text messages,
a health appointments service to manage doctor and dentist appointments for the individual,
a medicine reminders service to schedule medicine reminders for the individual,
a home services service to schedule home services for the individual,
a home security service to provide a security system for the individual,
a grocery shopping service to manage orders and deliveries of groceries to the individual,
an events service to provide updates on local events to the individual, or
a banking service to manage bills and finances of the individual.

20. The non-transitory computer-readable medium of claim 15, wherein the instructions further comprise:
one or more instructions that, when executed by the one or more processors, cause the one or more processors to:
cause the client device associated with the caregiver to display a user interface for receiving the configuration information; and
create the training set based on receiving the configuration information.

* * * * *

UNITED STATES PATENT AND TRADEMARK OFFICE
CERTIFICATE OF CORRECTION

PATENT NO. : 10,916,344 B2
APPLICATION NO. : 16/191363
DATED : February 9, 2021
INVENTOR(S) : Eriksson et al.

It is certified that error appears in the above-identified patent and that said Letters Patent is hereby corrected as shown below:

In the Claims

Column 23, Lines 2-3, Claim 2 change "plurality of client devices, about one of the one or more first activities;" to --plurality of client devices, about one of the one or more activities;--

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*